United States Patent
Johnsen

(10) Patent No.: US 9,345,564 B2
(45) Date of Patent: May 24, 2016

(54) REMOVABLE VENA CAVA FILTER HAVING PRIMARY AND SECONDARY STRUTS

(71) Applicant: COOK MEDICAL TECHNOLOGIES LLC, Bloomington, IN (US)

(72) Inventor: Jeppe Bøckhaus Johnsen, Froerup (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 245 days.

(21) Appl. No.: 13/832,405

(22) Filed: Mar. 15, 2013

(65) Prior Publication Data

US 2014/0277080 A1    Sep. 18, 2014

(51) Int. Cl.
*A61F 2/01* (2006.01)

(52) U.S. Cl.
CPC ............. *A61F 2/01* (2013.01); *A61F 2002/011* (2013.01); *A61F 2002/016* (2013.01); *A61F 2230/0058* (2013.01); *A61F 2230/0093* (2013.01)

(58) Field of Classification Search
CPC ....... A61F 2/00; A61F 2/01; A61F 2002/016; A61F 2230/0058; A61F 2002/011; A61F 2002/015; A61F 2002/018; A61F 2/013; A61F 2/82; A61F 5/441; A61F 17/221; A61F 2/06; A61F 2/07; A61B 17/2204; A61B 2017/2212; A61B 2017/2215; A61B 2018/004; A61B 2018/0041; A61B 2018/0046; A61B 2018/00375; A61B 17/1219; A61B 17/1213; A61B 17/1218; A61B 17/12122; A61B 17/12145
USPC ....................................................... 606/200
See application file for complete search history.

(56) References Cited

U.S. PATENT DOCUMENTS

| 4,425,908 | A  |   | 1/1984  | Simon |
| 4,688,553 | A  |   | 8/1987  | Metals |
| 5,634,942 | A  |   | 6/1997  | Chevillon et al. |
| 5,669,933 | A  | * | 9/1997  | Simon et al. ................... 600/200 |
| 5,836,968 | A  |   | 11/1998 | Simon et al. |
| 5,836,969 | A  |   | 11/1998 | Kim et al. |
| 6,517,559 | B1 |   | 2/2003  | O'Connell |
| 7,575,584 | B2 |   | 8/2009  | WasDyke |
| 7,757,692 | B2 |   | 7/2010  | Alferness et al. |
| 7,799,049 | B2 |   | 9/2010  | Ostrovsky et al. |
| 7,909,847 | B2 |   | 3/2011  | McGuckin, Jr. et al. |
| 7,998,164 | B2 |   | 8/2011  | Saholt et al. |
| 8,029,529 | B1 |   | 10/2011 | Chanduszko |
| 8,092,484 | B2 |   | 1/2012  | Kashkarov et al. |
| 8,105,349 | B2 |   | 1/2012  | Hendriksen et al. |
| 8,177,805 | B2 |   | 5/2012  | Alferness |
| 2012/0184987 | A1 | * | 7/2012  | Sirota ............................ 606/200 |

* cited by examiner

*Primary Examiner* — Jonathan W Miles
*Assistant Examiner* — George J Ulsh
(74) *Attorney, Agent, or Firm* — Brinks Gilson & Lione

(57) ABSTRACT

A removable filter has a hub defining a waist and a longitudinal filter axis; a plurality of primary struts extending from a first axial side of the hub, and a plurality of secondary struts extending from a second axial side of the hub opposite the first axial side. The secondary struts form a radially outward arc extending from the hub over an angle of at least about 180° in the expanded state, preferably between about 190° and about 270°. A retrieval coil with a proximal end fastened to an elongated wire has several longitudinally offset windings. The retrieval coil is preferably more rigid than the primary struts. The coil may preferably have a distal winding with an inner diameter that is greater than the diameter of the hub and smaller than the diameter of the filter in the expanded state.

19 Claims, 6 Drawing Sheets

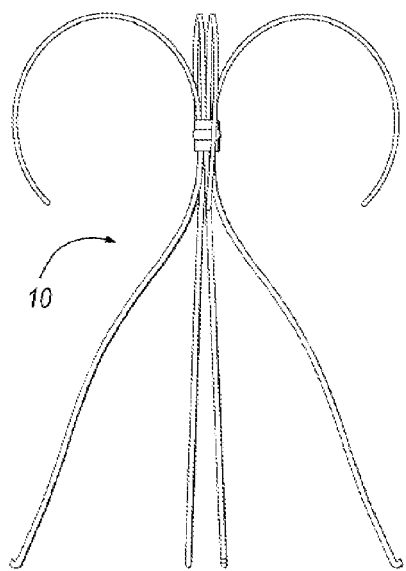
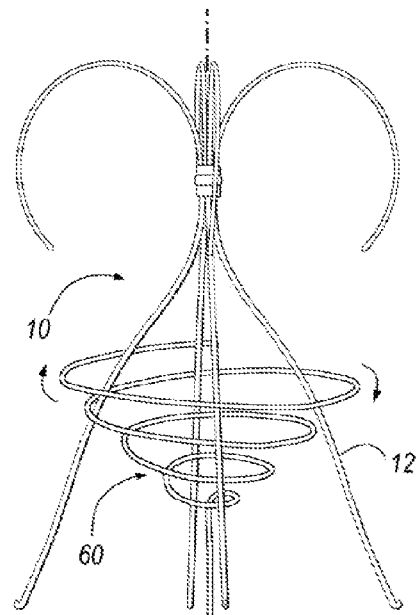
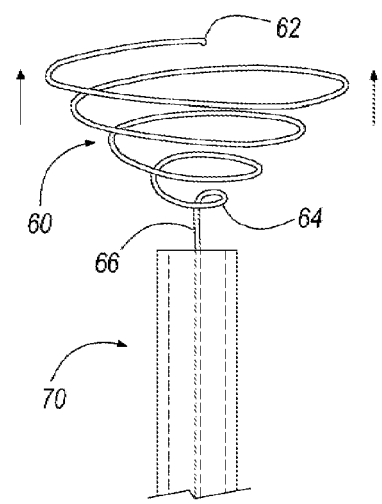
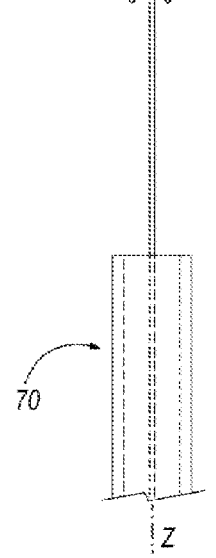
*Fig. 3a*  *Fig. 3b*

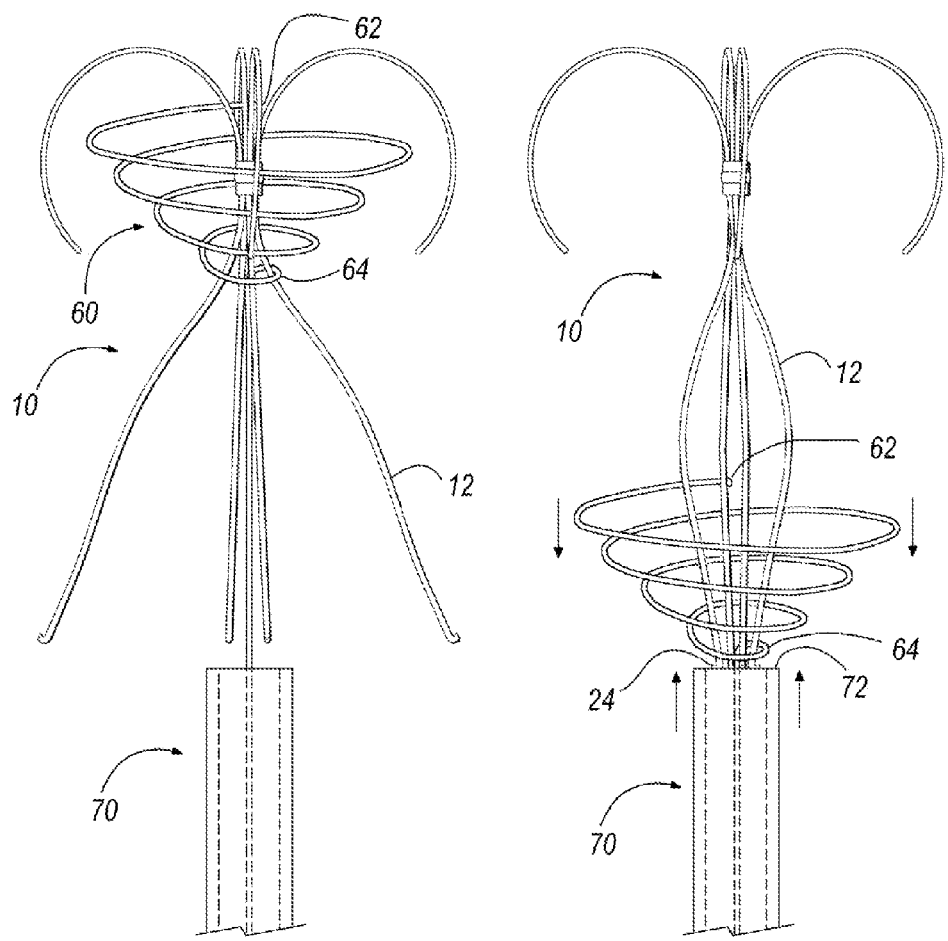
*Fig. 3c*  *Fig. 3d*

REMOVABLE VENA CAVA FILTER HAVING PRIMARY AND SECONDARY STRUTS

FIELD OF THE INVENTION

The present invention relates to medical devices. More particularly, the invention relates to a removable vena cava clot filter that can be percutaneously placed in and removed from the vena cava of a patient.

BACKGROUND OF THE INVENTION

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

After deployment of a generally conical filter in a patient, the filter may eventually end up in a tilted position. Proliferating intimal cells begin to accumulate around the filter parts which contact the wall of the vessel. After a length of time, such ingrowth prevents removal of the filter without risk of trauma so that the filter is permanently left in the patient.

Moreover, conventional filters commonly become off-centered or tilted with respect to the hub of the filter and the longitudinal axis of the vessel in which it has been inserted. As a result, the filter including the hub and the retrieval hook engage the vessel wall along their lengths and potentially become endothelialized therein. As a result, the filter becomes a permanent implant in a shorter time period than otherwise.

Further improvements may be made related to the retrieval of vena cava filters.

SUMMARY OF THE INVENTION

One embodiment of the present invention generally provides a removable vena cava filter configured for reducing the risk of a tilted implantation.

According to a first aspect of the invention, a removable filter has a collapsed state and an expanded state for capturing thrombi in a blood vessel. The filter includes a hub defining a waist and a longitudinal filter axis; a plurality of primary struts extending from a first axial side of the hub axially away from the hub and radially outward in the expanded state; and a plurality of secondary struts extending from a second axial side of the hub opposite the first axial side. The secondary struts form a radially outward arc extending from the hub over an angle of at least about 180° in the expanded state. The arc preferably extends from the hub over an angle of between about 190° and about 270° in the expanded state. This arrangement allows for a tangential engagement of the secondary struts with the vessel wall, while also allowing for a non-traumatic retrieval of the filter.

According to another aspect of the invention, a retrieval coil with a proximal end fastened to an elongated wire has several longitudinally offset windings. The retrieval coil is preferably more rigid than the primary struts. The retrieval coil may, for example, have a generally conical shape distally expanding from a proximal end. Alternatively, or additionally, at least a distal portion of the retrieval coil may have a generally cylindrical shape. The coil may preferably have a distal winding with an inner diameter that is greater than the diameter of the hub and smaller than the diameter of the filter in the expanded state.

Further details and benefits of the present invention become apparent from the following description of drawings illustrating preferred embodiment of the invention. The drawings are presented herein solely for illustrative purposes and are not intended to limit the scope of the present invention.

BRIEF DESCRIPTION OF THE DRAWINGS

FIG. 3a shows a first step of retrieving the vena cava filter of FIG. 1 with a first embodiment of a removal coil;

FIG. 3b shows a second step of retrieving the vena cava filter of FIG. 1;

FIG. 3c shows a third step of retrieving the vena cava filter of FIG. 1;

FIG. 3d shows a fourth step of retrieving the vena cava filter of FIG. 1;

DETAILED DESCRIPTION OF THE DRAWINGS

Figure 2:
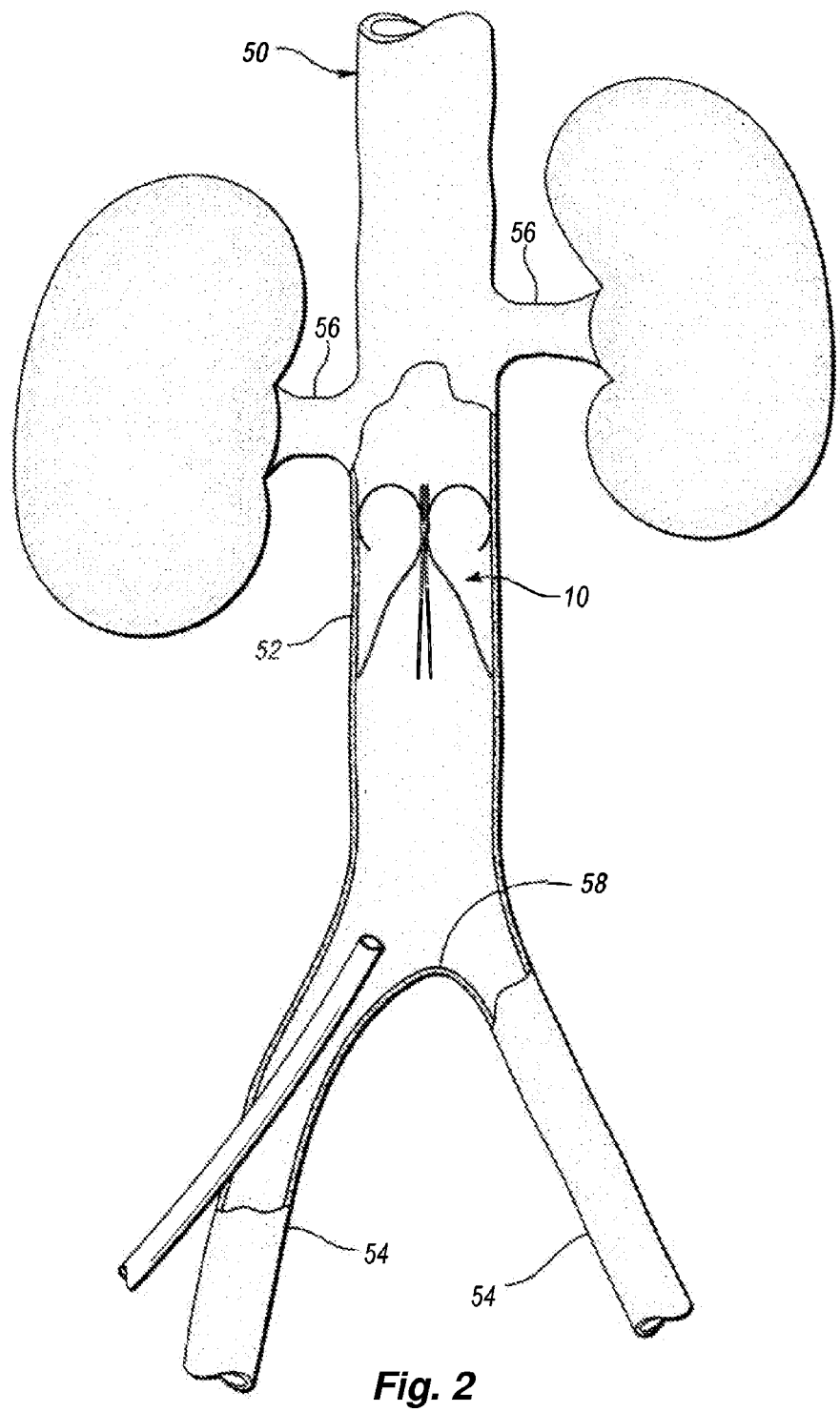
FIG. 2 is an illustration of the anatomy of the renal veins, the iliac veins, and the vena cava in which the a vena cava filter of FIG. 1 is deployed.

In accordance with one embodiment of the present invention, FIG. 2 illustrates a vena cava filter 10 implanted in the vena cava 50 for the purpose of lysing or capturing thrombi carried by the blood flowing through the iliac veins 54 toward the heart and into the pulmonary arteries. As shown, the iliac veins merge at juncture 58 into the vena cava 50. The renal veins 56 from the kidneys 62 join the vena cava 50 downstream of juncture 58. The portion of the vena cava 50, between the juncture 58 and the renal veins 56, defines the inferior vena cava 52 in which the vena cava filter 10 has been percutaneously deployed through one of the femoral veins. Preferably, the vena cava filter 10 has a length smaller than the length of the inferior vena cava 52. If the lower part of the filter extends into the iliac veins, filtering effectiveness will be compromised and if the filter wires cross over the origin of the renal veins the filter wires might interfere with the flow of blood from the kidneys.

Figure 1:
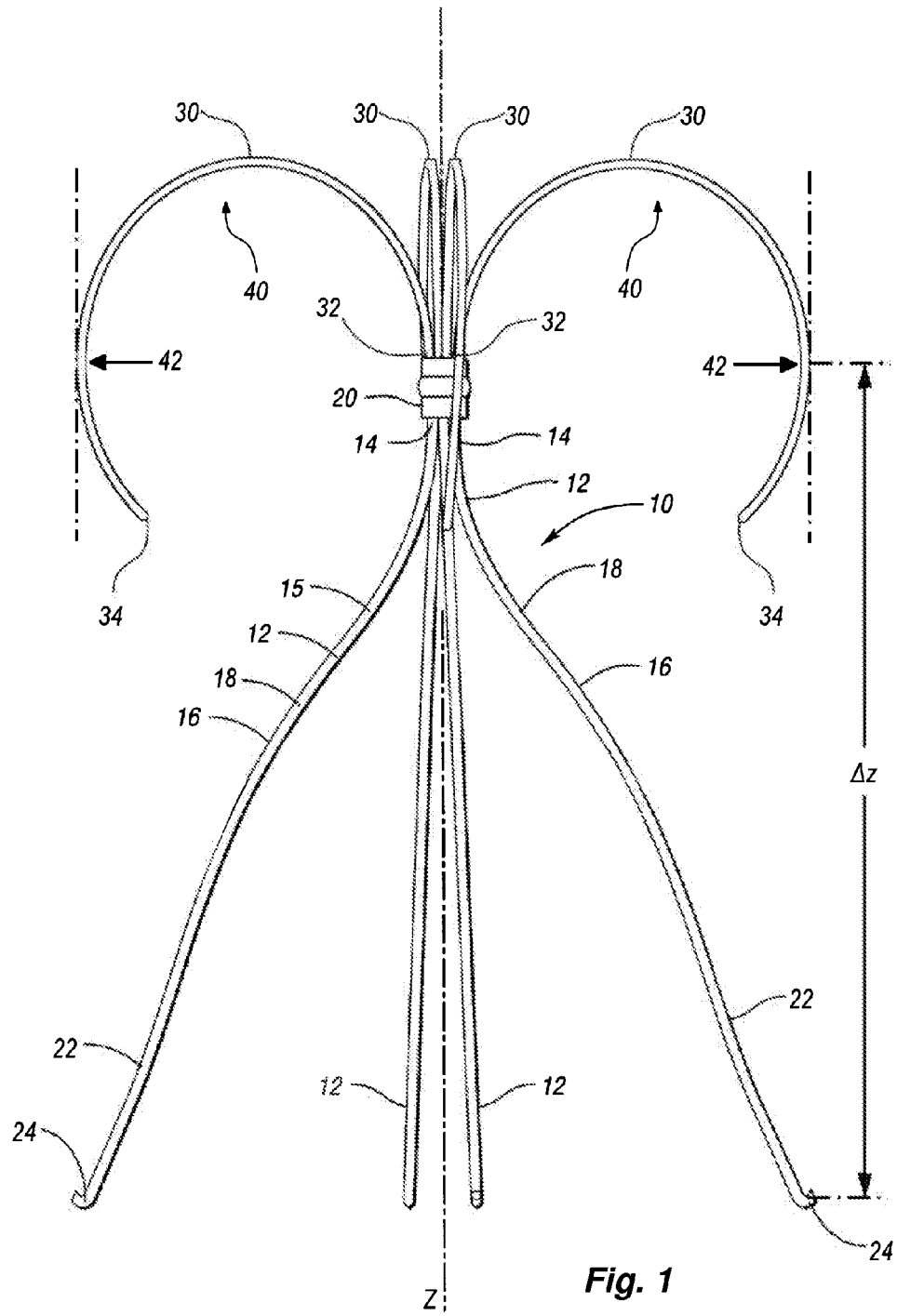
FIG. 1 is a side view of a first embodiment of a vena cava filter according to the present invention.

This embodiment of the present invention will be further discussed with reference to FIGS. 1 and 3a through 3f, in which filter 10 is shown. FIG. 1 illustrates filter 10 in an expanded state and comprising four primary struts 12 each having first ends that emanate from a hub 20. Hub 20 attaches by crimping connected primary ends 14 of primary struts 12 together in a compact bundle along a central or longitudinal axis Z of the filter. The hub 20 has a minimal diameter for the size of wire used to form the struts.

Preferably, the primary struts 12 are formed of a superelastic material, stainless steel wire, Nitinol, cobalt-chromium-nickel-molybdenum-iron alloy, or cobalt chrome-alloy or any other suitable superelastic material that will result in a self-opening or self-expanding filter. In this embodiment, the primary struts 12 are preferably formed from wire having a round cross-section with a diameter of at least about 0.015 inches. Of course, it is not necessary that the primary struts have a round or near round cross-section. For example, the primary struts 12 could take on any shape with rounded edges to maintain non-turbulent blood flow therethrough.

As shown in FIGS. 1, 2, and 3*a*, each primary strut 12 includes an arcuate segment 16 having a soft S-shape. Each arcuate segment 16 is formed with a first curved portion 18 that is configured to softly bend away from the longitudinal or central axis Z of the filter 10 and a second curved portion 22 that is configured to softly bend toward the longitudinal axis of the filter 10. Due to the soft bends of each arcuate segment 16, a prominence or a point of inflection on the primary strut 12 is substantially avoided to aid in non-traumatically engaging the vessel wall.

As shown in FIG. 1, the primary struts 12 terminate at anchor hooks 24 that will anchor in the vessel wall when the filter 10 is deployed at a delivery location in the blood vessel. The primary struts 12 are configured to move between an expanded state for engaging the anchor hooks 24 with the blood vessel and a collapsed state for filter retrieval or delivery. In the expanded state, each arcuate segment 16 extends arcuately outward along a longitudinal axis Z from the connected primary end 14 to the anchor hook 24. In this embodiment, the primary struts 12 do not have any curves in the circumferential direction and avoid entanglement with other struts 12.

When the filter 10 is deployed in a blood vessel, the anchor hooks 24 engage the walls of the blood vessel to define a first axial portion to secure the filter in the blood vessel. The anchor hooks 24 prevent the filter 10 from migrating from the delivery location in the blood vessel where it has been deposited. The primary struts 12 are shaped and dimensioned such that, when the filter 10 is freely expanded, the filter 10 has a diameter of between about 25 mm and 45 mm and a length of between about 3 cm and 7 cm. For example, the filter 10 may have a diameter of about 35 mm and a length of about 5 cm. The primary struts 12 have sufficient spring strength that, when the filter is deployed, the anchor hooks 24 will anchor into the vessel wall.

In this embodiment, the filter 10 includes a plurality of secondary struts 30 having connected secondary ends 32 that also extend from hub 20 as shown in FIG. 1. In the embodiment shown in FIGS. 1 through 3*f*, four secondary struts 30 emerge from the hub 20 at an axial side opposite the primary struts 12. In the following, the axial side of the hub 20 from which the primary struts 12 extend will be called primary side, and the axial side of the hub 20 from which the secondary struts 30 extend will be called secondary side.

Hub 20 is stationarily attached to the connected secondary ends 32 and the connected primary ends 14. The connection between the hub 20 and ends 14 and 32 may, for example, be accomplished by crimping, by laser welding, or any other suitable method creating a durable connection. In this embodiment, each primary strut 12 has one secondary strut 30 arranged side-by-side and distributed around the circumference of the hub 20. The secondary struts 30 extend from the connected secondary ends 32 to free ends 34 to longitudinally align the filter 10 in the expanded state in the blood vessel. Like the primary struts 12, the secondary struts 30 are free of any circumferential curves and avoid entanglement with other struts.

In this embodiment, each of the secondary struts 30 is formed of an ellipsoidal arc 40 extending away from the secondary side of hub 20, radially outward away from the longitudinal axis Z, and axially backward toward the primary side of the hub 20. The secondary struts preferably describe an arc along over 180° so that the free ends 34 are in a position radially inward from the radially outermost portions of the secondary struts 30. In other words, the secondary struts 30 have an expanded state, in which each of the second struts 30 forms an outward curl so that the arcs 40 of all secondary struts 30 envelope a generally toroidal shape with a generally elliptical cross-section and with a central axis coinciding with the longitudinal axis Z.

The secondary struts 30 may be made from the same type of material as the primary struts 12. However, the secondary struts 30 may have a smaller diameter than the primary struts 12, e.g. at least about 0.012 inches. The hub 20 is preferably made of the same material as the primary struts 12 and secondary struts 30 to minimize the possibility of galvanic corrosion or molecular changes in the material due to welding.

The primary struts 12 and secondary struts 30 may be formed from any suitable material that will result in a self-opening or self-expanding filter 10, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the transition temperature is chosen to be slightly below normal body temperature of humans, which is about 98.6° F. Thus, when the filter 10 is deployed in the vena cave 52 and exposed to normal body temperature, the alloy of the struts 12 and 30 will transform to austenite, that is, the remembered state, which for the present invention is an expanded configuration when the filter 10 is deployed in the blood vessel. To remove the filter 10, the filter 10 is cooled to transform the material to martensite which is more ductile than austenite, making the struts 12 and 30 more malleable. As such, the filter 10 can be more easily collapsed and pulled into the sheath for removal.

In other embodiments, both the primary struts 12 and the secondary struts 30 are made from Nitinol with a transition temperature that is above normal body temperature of humans, which is about 98.6° F. Thus, when the filter is deployed in the vena cave and exposed to normal body temperature, the struts are in the martensitic state so that the struts are sufficiently ductile to bend or form into a desired shape, which for the present invention is an expanded configuration. To remove the filter, the filter is heated to transform the alloy to austenite so that the filter becomes rigid and returns to a remembered state, which for the filter is a collapsed configuration.

Notably, other materials allowing for a delivery and removal of the filter 10 by elastic deformation are well within the scope of the present invention.

When freely expanded, the secondary struts 30 will expand radially outward to a diameter of about 25 mm to 45 mm. For example, the secondary struts 30 may expand radially outward to a diameter of between about 35 mm and 45 mm. Generally, the expanded diameter of the secondary struts 30 is similar to the expanded diameter of the primary struts 12 in the sense that the diameters are chosen relative to each other to provide support for identical vessel diameters. The diameter spanned by the secondary struts 30 is approximately twice the radial diameter of the curve described by the arcs 40.

Thus the arcs 40 each have a turn radius of between about 12 mm and about 23 mm, preferably between about 17 mm and about 22 mm.

The secondary struts 30 function to stabilize the position of the filter 10 about the center of the blood vessel in which it is deployed. As evident from FIG. 1, each of the secondary struts 30 includes a radially outer portion 42 extending parallel to the longitudinal axis Z. These radially outer portions 42 tangentially engage the vessel wall of the vena cava after deployment as can be seen in FIG. 2. Thus, the secondary struts 30 contact the vessel wall without perforating it. The arc 40 of the secondary struts 30 extends over an angle of at least about 180°. The arc 40 may extend over up to about 270° or even more. But while it is desirable that the arc is long enough to place the free ends 34 in a location that is not in contact with the vessel wall in the expanded state, any further length of the secondary struts 30 is unnecessary and increases the collapsed length of the filter 10 without need. Thus, the arc preferably extends over an angle between about 200° and 270°.

As a result, the filter 10 has two sets of struts engaging the vessel wall of the blood vessel in locations that are longitudinally apart by an offset Δz. The offset Δz may be close to or even greater than the longitudinal distance of the anchor hooks 24 from the hub 20. Compared to smaller offsets between primary and secondary struts, the larger Δz has the advantage that a deformation or displacement of a strut 12 or 30 has a smaller influence on the alignment angle of the longitudinal axis Z relative to the direction of the inferior vena cava 52. Thus, the filter alignment becomes more robust.

As briefly indicated above, the length of the filter 10 in the collapsed state is defined by the sum of the lengths of the primary struts 12 and of the straightened secondary struts. In the expanded state, the length of the filter 10 is approximately defined by the sum of the longitudinal component of the primary struts 12 and the radius of the arc 40 described by the secondary struts 30.

Figure 5:
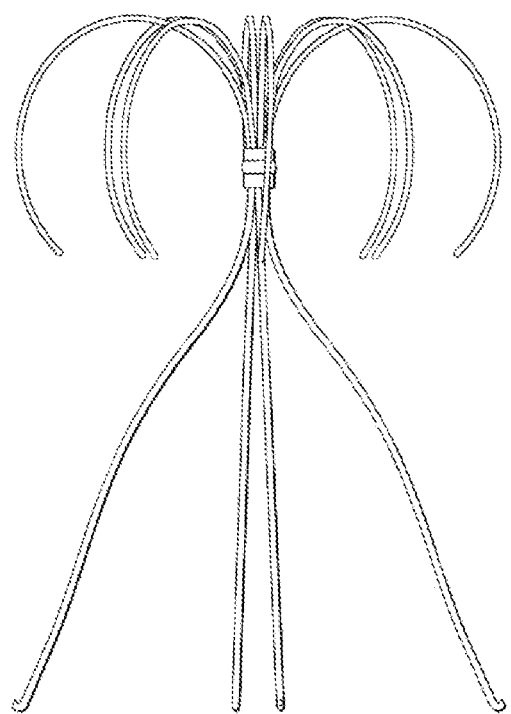
FIG. 5 shows a second embodiment of a vena cava filter.

The diameter of the hub 20 is defined by the size of a bundle containing either the primary struts 12 on the primary side or the secondary struts 30 on the secondary side. In this embodiment, the primary struts define the diameter of the hub 20 due to the reduced cross-section of each secondary strut 30. If, as shown in FIG. 5, the number of secondary struts is increased, the secondary struts may determine the hub diameter. Thus, the diameter of the hub corresponds to a cross-section that accommodates the larger one of the cross-sections of the strut bundles.

In this embodiment, each arcuate segment 16 has a thickness of at least about 0.015 inch and a tensile strength of between about 285,000 pounds per square inch (psi) and 330,000 psi. Each anchor hook 24 is integral with the arcuate segment 16 and has the thickness and the tensile strength of the arcuate segment 16. Each secondary strut 30 has a thickness of at least about 0.012 inch and a tensile strength of between about 285,000 psi and 330,000 psi.

In this embodiment of the present invention, it is to be noted that the filter 10 may be delivered or retrieved by any suitable introducer (delivery or retrieval) tube. However, it is preferred that the introducer tube has an inside diameter of between about 4.5 French and 16 French, and more preferably between about 6.5 French and 14 French.

For example, the filter 10 may be inserted from the femoral side through the proximal end of a delivery tube with the secondary side leading. During deployment, the secondary struts 30 expand first to centralize or balance the filter within the vessel by. When the free ends of the secondary struts emerge from the distal end of the delivery tube, the secondary struts 30 expand and tangentially roll along the vessel wall to the expanded position as shown in FIGS. 1, 2, and 3a. The filter 10 may then pushed further by a pusher wire until it is fully deployed. Alternatively, the delivery tube may be withdrawn to expel the primary struts 12 as shown in FIG. 2.

When the filter 10 is fully expanded in the vena cava, the anchor hooks 24 of the primary struts 12 and the radially outer portions 42 of the secondary struts 30 are in engagement with the vessel wall. The anchor hooks 24 of the primary struts 12 have anchored the filter 10 at the location of deployment in the vessel, preventing the filter 10 from moving with the blood flow through the vessel. The secondary struts 30 reduce the risk of tilting by keeping the hub 20 centered within the body vessel. As a result, the filter 10 is supported by two sets of struts 12 and 30 that are spaced axially along the length of the filter by offset Δz.

FIGS. 3a through 3f illustrate steps of a retrieval procedure for removing the filter 10 from the inferior vena cava 52. In this procedure, a removal sheath 70 approaches the filter 10 from the primary side.

As shown in FIG. 3a, a retrieval coil 60 is introduced via a proximally attached push wire 66 through the sheath 70 into the inferior vena cava 52 to a position, in which the retrieval coil 60 longitudinally overlaps with the primary struts 12.

As illustrated in FIG. 3b, the retrieval coil is then rotated about the longitudinal axis Z in a rotational direction that engages the distal coil end 62 with the primary struts 12 by leading the distal coil end 62 from the interior of the filter 10 to the exterior of the filter 10 and around the primary struts 12. In order for the coil to engage the primary struts 12, at least the most distal coil windings have an inner diameter that is greater than the diameter of the hub 20 and smaller than the diameter of the filter 10 in the expanded state.

The rotation of the retrieval coil 60 is continued until the most proximal portion 64 of the retrieval coil as shown in FIG. 3c, or until at least several windings of the retrieval coil extend on the exterior of the filter 10.

As indicated in FIG. 3d, the retrieval coil 60 is then longitudinally moved relative to the filter 10 and the sheath 70 such that the retrieval coil 60 is retracted toward the sheath 70. Optionally, a counter force may be applied to the filter, for example with a separate push wire, to facilitate the longitudinal move of the coil windings down the primary struts 12. As the retrieval coil 60 glides along the primary struts 12, the primary struts 12 are deflected and gradually collapsed.

Preferably, the retrieval coil 60 has at least one proximal winding that has a smaller outer diameter than the inner diameter of the distal end 72 of the sheath so that at least the first coil winding can enter the sheath 70 without deformation. The anchor hooks 24 thus can only expand to a diameter smaller than the inner diameter of the sheath 70 and can be introduced into the distal end 72 of the sheath 70. When the most proximal one of the coil windings extending on the exterior of the filter 10 reaches the anchor hooks 24, at least one of the anchor hooks 24 of the primary struts 12 catches onto the winding of the retrieval coil 60. At this point, the sheath 70 may be distally advanced toward the filter hub 20 while the retrieval coil 60 and the filter 10 remain stationary. Alternatively, the coil 60 and the filter 10 may be proximally withdrawn, or both the sheath 70 and the combination of retrieval coil 60 and filter 10 may be moved relative to each other.

Figure 3E:
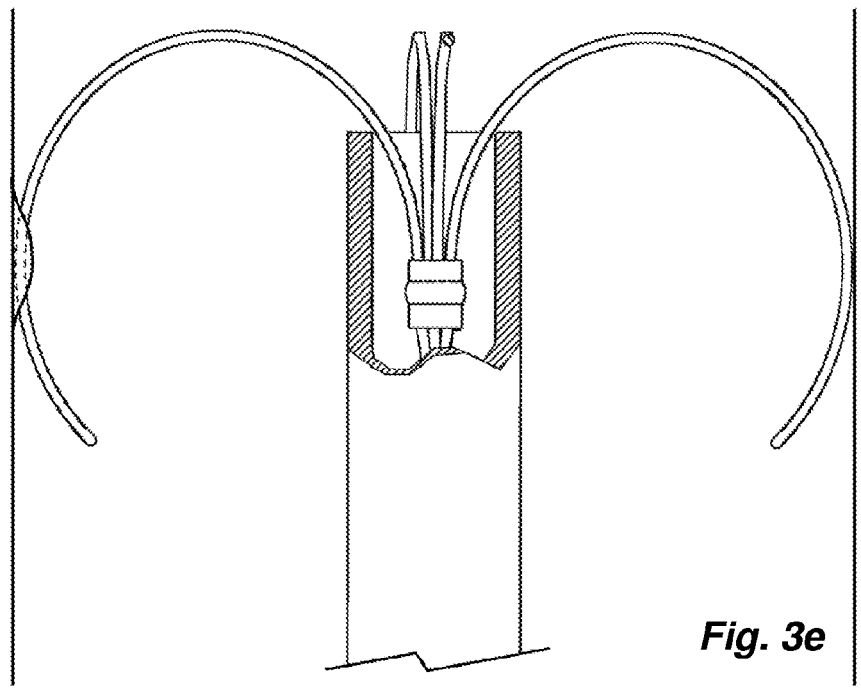
FIG. 3e shows a fifth step of retrieving the vena cava filter of FIG. 1.

Eventually, the primary struts 12 and the hub 20 are accommodated in the sheath as shown in FIG. 3e. As the distal end 72 of the sheath 70 passes the hub 20, the distal end 72 contacts the secondary struts 30 in a location 74 that corresponds to the inner diameter of the sheath 70. The location 74 is preferably located in a section of the arc 40, in which the arc still extends axially away from the hub 20 so that any forces exerted on the secondary struts 20 urges the secondary struts 20 to straighten. Thus, the interior diameter of the sheath 70 at the distal end 72 is preferably smaller than half of the filter diameter in the expanded state.

A further proximal withdrawal of the retrieval coil 60 with the filter 10 causes a retraction of the secondary struts 30 along the arc 40. As evident from FIG. 3e, this is particularly beneficial if, as indicated on the left side of the drawing, the radially outer portion 42 of the secondary strut 30 has been overgrown with body tissue. The secondary strut 30 is retracted along its own arc 40 so that the secondary strut 30 traces itself and no new trauma in the form of punctures or scratches is created.

Figure 3F:
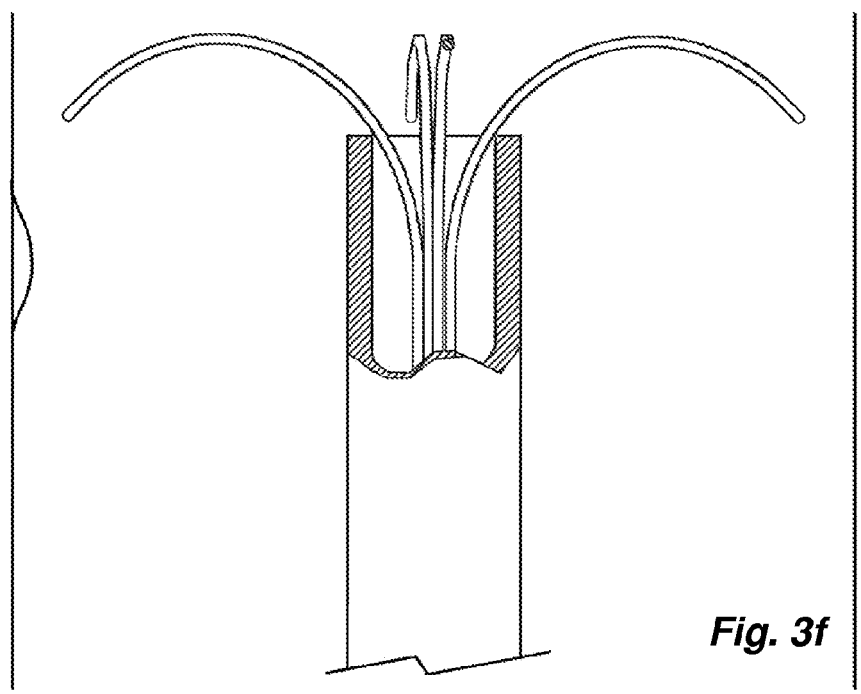
FIG. 3f shows a fourth step of retrieving the vena cava filter of FIG. 1.

The arc 40, while retaining its curvature, becomes shorter until the free ends 34 come out of contact with the vessel wall and with any overgrowth as shown in FIG. 3f. Finally, the filter 10 is entirely accommodated in the sheath 70 (not shown), which then can be retracted from the patient's body. As previously noted, the retrieval procedure only requires a relative movement between the retrieval coil 60 and the sheath 70. Thus, instead of withdrawing the retrieval coil 60, it is additionally or alternatively possible to advance the sheath 70 over the filter 10.

In the embodiment of FIGS. 3a through 3f, the retrieval coil 60 has windings that envelope a generally cone-shaped volume. The most distal winding of the retrieval coil 60 has the largest diameter. The coil diameter is continuously reduced toward the proximal end 64 of the coil 60. The proximal end 64 is connected to a longitudinal push wire 66 suitable for transmitting longitudinal and rotational forces. The distal coil diameter is larger than the inner diameter of the sheath 70, but smaller than the expanded diameter of the filter. The proximal coil diameter is smaller than the inner diameter of the sheath 70. This proximal coil diameter ensures that the proximal ends of the primary struts are sufficiently collapsed to enter the distal end 72 of the sheath 70. The retrieval coil 60 is preferably stiffer than the primary struts, but flexible enough the straighten enough to be delivered and withdrawn through the sheath 70. The retrieval coil may include or consist of any biocompatible material that can provide the desired properties. Suitable materials include stainless steel, other metals, or even plastics. The coil may be coated with a material that enhance the slidability and resist attachment to the body vessel, such as PTFE.

The distal end 62 of the coil 60 may optionally be formed as a radially inward engagement hook. While the retrieval coil 60 is retracted into the sheath, engagement hook may catch onto one of the primary struts so that the retrieval coil cannot simply straighten and slip into the sheath 70 past the filter 10 without taking the filter 10 along.

Figure 4:
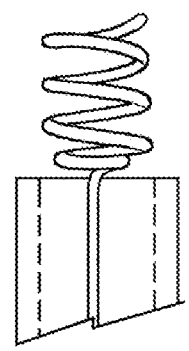
FIG. 4 shows a second embodiment of a removal coil.

FIG. 4 shows an alternative embodiment of a retrieval coil 160. The retrieval coil 160 has a distal cylindrical portion 162 and a short proximal conical portion 164. The conical portion 164 is optional, and the longitudinal wire 166 may be directly attached to the cylindrical portion 162. The outer diameter of the retrieval coil 160 is dimensioned to be smaller than the inner diameter of the sheath 70. Still, in order for the coil to engage the primary struts 12, the cylindrical portion 162 has an inner diameter that is greater than the diameter of the hub 20 and smaller than the diameter of the filter 10 in the expanded state.

Thus, the retrieval coil 160 does not have to undergo any deformation for accommodation inside the catheter 70. Accordingly, the retrieval coil 160 may be more rigid than the retrieval coil 60 of FIGS. 3a through 3f. Because the retrieval coil 160 need not be deformed during the retrieval of the filter 10, an engagement hook at the distal end is unnecessary. Otherwise, the retrieval method of FIGS. 3a through 3f is applicable to the use of the retrieval coil 160 in analogy.

In another embodiment shown in FIG. 5, a filter 110 includes four primary struts 12 and eight secondary struts 30 that extend from a hub 20. The filter 110 of FIG. 5 may have thinner secondary struts 30 than the filter 10 of FIGS. 1 through 3. Otherwise, the same considerations apply to its structure, delivery, and removal as to filter 10 of FIGS. 1 through 3. While only two examples of filters 10 and 110 with different numbers of struts have been shown in the drawings, the number of both the primary struts 12 and the secondary struts 30 can vary nearly arbitrarily. Preferably, the number of primary struts 12 and the number of secondary struts 30 are both greater than two. The number of primary struts 12 and the number of secondary struts 30 do not depend on each other because the primary struts 12 and the secondary struts extend from opposite sides of the hub 20.

While the present invention has been described in terms of preferred embodiments, it will be understood, of course, that the invention is not limited thereto since modifications may be made to those skilled in the art, particularly in light of the foregoing teachings.

What is claimed is:

1. A removable filter assembly comprising a filter having a collapsed state and an expanded state for capturing thrombi in a blood vessel, the filter including: a hub defining a waist and a longitudinal filter axis; a plurality of primary struts extending from a first axial side of the hub axially away from the hub and radially outward and terminating in primary free ends in the expanded state; and a plurality of secondary struts extending from a second axial side of the hub opposing the first axial side, the plurality of secondary struts extending axially away from the hub and axially away from the primary struts in a strut portion adjoining the hub, and terminating in secondary free ends which, in the expanded state, point toward the longitudinal filter axis, the secondary struts forming a radially outward arc extending from the hub over an angle of at least about 180° in the expanded state.

2. The assembly of claim 1, wherein the arc extends from the hub over an angle of between about 190° and about 270° in the expanded state.

3. The assembly of claim 1, wherein each secondary strut is formed of a superelastic material, stainless steel wire, Nitinol, cobalt-chromium-nickel-molybdenum-iron alloy, or cobalt-chrome alloy.

4. The assembly of claim 1, wherein the secondary struts are free of any circumferential curves relative to the longitudinal filter axis.

5. The assembly of claim 1, wherein each arc has a turn radius of between about 12 mm and about 25 mm.

6. The assembly of claim 1, wherein the secondary struts have smaller diameters than the primary struts.

7. The assembly of claim 1, wherein the primary struts and the secondary struts are formed of shape memory alloy with a transition temperature.

8. The assembly of claim 7, wherein the primary struts and the secondary struts collapse to the collapsed state when the temperature of the primary struts and the secondary struts is about equal to or greater than the transition temperature.

9. The assembly of claim 7, wherein the primary struts and the secondary struts expand to the expanded state when the temperature of the primary struts and the secondary struts is about equal to or greater than the transition temperature.

10. The assembly of claim 1, further comprising a retrieval coil with a proximal end fastened to an elongated wire, the retrieval coil having several axially offset windings.

11. The assembly of claim 10, wherein the retrieval coil is made of a material that is more rigid than the primary struts.

12. The assembly of claim 10, wherein the retrieval coil has a generally conical shape distally expanding from a proximal end.

13. The assembly of claim 10, wherein at least a distal portion of the retrieval coil has a generally cylindrical shape.

14. The assembly of claim 10, wherein the coil has a distal winding with an inner diameter that is greater than the diameter of the hub and smaller than the diameter of the filter in the expanded state.

15. The assembly of claim 10, further comprising a sheath for inserting the retrieval coil into a body vessel.

16. The assembly of claim 15, wherein the sheath has an interior diameter that is greater than the diameter of the hub and smaller than the diameter of the filter in the expanded state.

17. The assembly of claim 15, wherein the sheath has an interior diameter greater than the outer diameter of at least a most proximal winding of the retrieval coil.

18. The assembly of claim 17, wherein the interior diameter of the sheath is greater than the diameters of all windings of the retrieval coil.

19. The assembly of claim 17, wherein the interior diameter of the sheath is smaller than half of the filter diameter in the expanded state.

\* \* \* \* \*